(12) United States Patent
Nuzzio

(10) Patent No.: US 8,361,411 B2
(45) Date of Patent: Jan. 29, 2013

(54) TOOL FOR SENSOR ARRANGEMENT WITH SNAP-OFF SEGMENTS

(76) Inventor: Donald B. Nuzzio, Ringoes, NJ (US)

( * ) Notice: Subject to any disclaimer, the term of this patent is extended or adjusted under 35 U.S.C. 154(b) by 31 days.

(21) Appl. No.: 13/134,545

(22) Filed: Jun. 8, 2011

(65) Prior Publication Data

US 2011/0308943 A1 Dec. 22, 2011

Related U.S. Application Data

(63) Continuation of application No. PCT/US2010/003145, filed on Dec. 10, 2010.

(60) Provisional application No. 61/283,996, filed on Dec. 10, 2009.

(51) Int. Cl.
*G01N 27/00* (2006.01)
(52) U.S. Cl. ..... 422/401; 422/413; 422/430; 422/82.01; 204/400
(58) Field of Classification Search .................. 422/401, 422/413, 430, 82.01; 204/400
See application file for complete search history.

(56) References Cited

U.S. PATENT DOCUMENTS 5,460,710 A * 10/1995 Williams et al. .............. 205/780

* cited by examiner

*Primary Examiner* — Lyle Alexander
(74) *Attorney, Agent, or Firm* — Rohm & Monsanto, PLC

(57) ABSTRACT

A tool for a sensor includes a first portion having an elongated channel that extends therealong for accommodating the sensor, and a second portion with an end slot that accommodates an end portion of the sensor, the sensor having one or more wire electrodes embedded between two substrates. One or both of the substrates has transaxial scoring for facilitating the snapping off of segments to expose a clean portions of the wire electrodes. One or both of the tool portions has a rounded end portion. The end slot of the second portion is dimensioned to correspond to an axial dimension of a segment that is to be snapped off from the sensor. The first tool portion has a shoulder and handle portions, the shoulder portion having a greater thickness than the handle portion, and the handle portion having a thickness that is less than the width of the sensor.

12 Claims, 5 Drawing Sheets

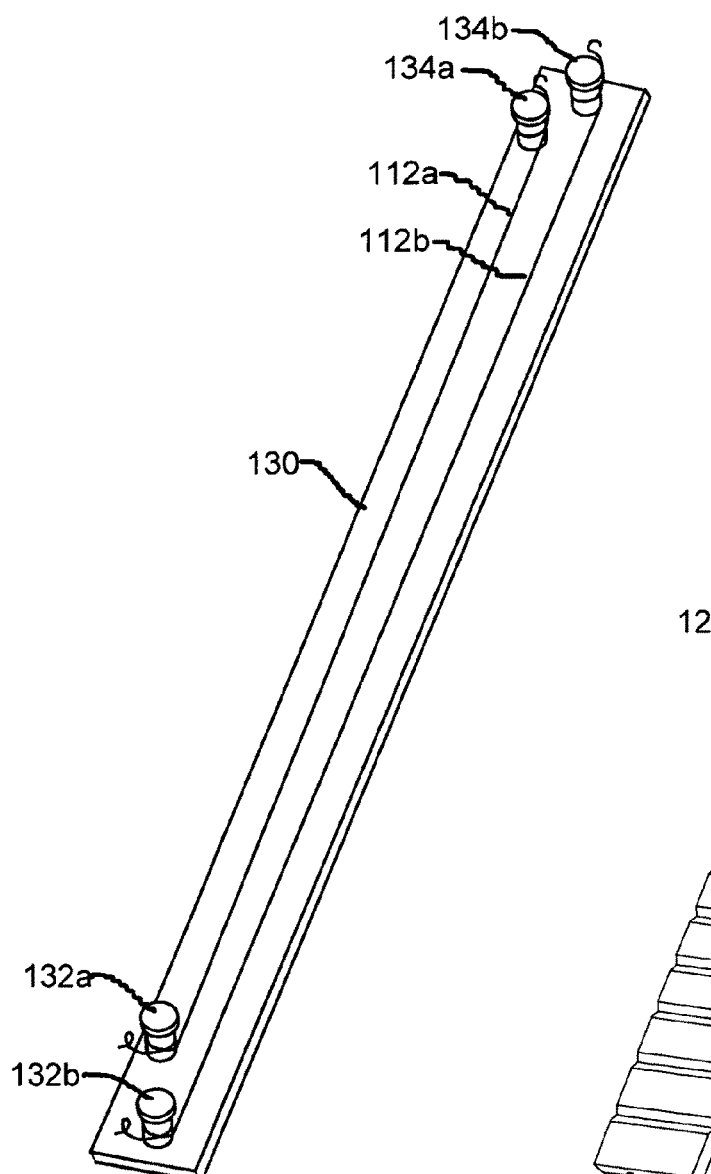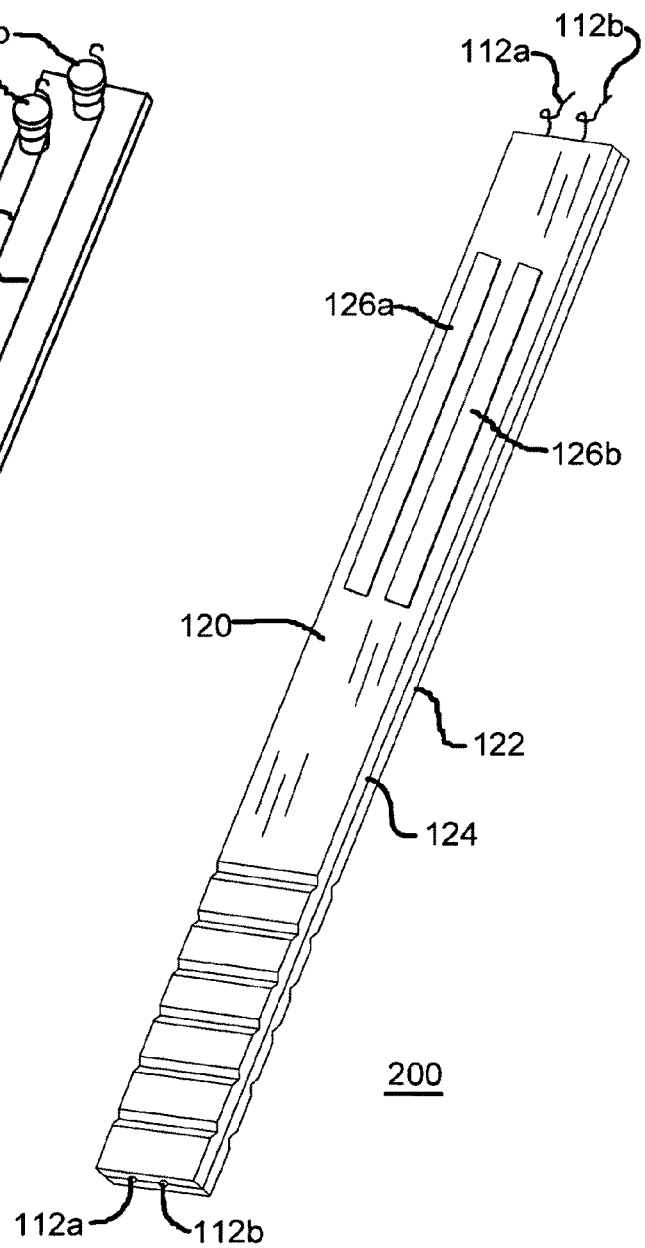

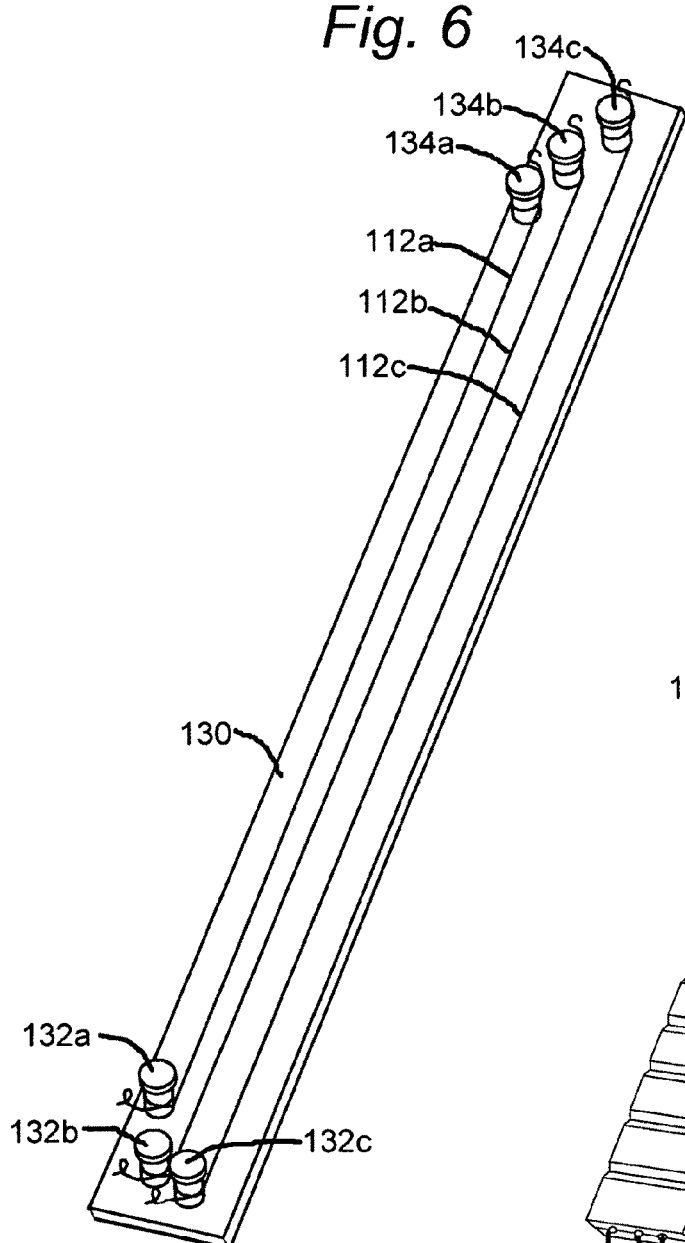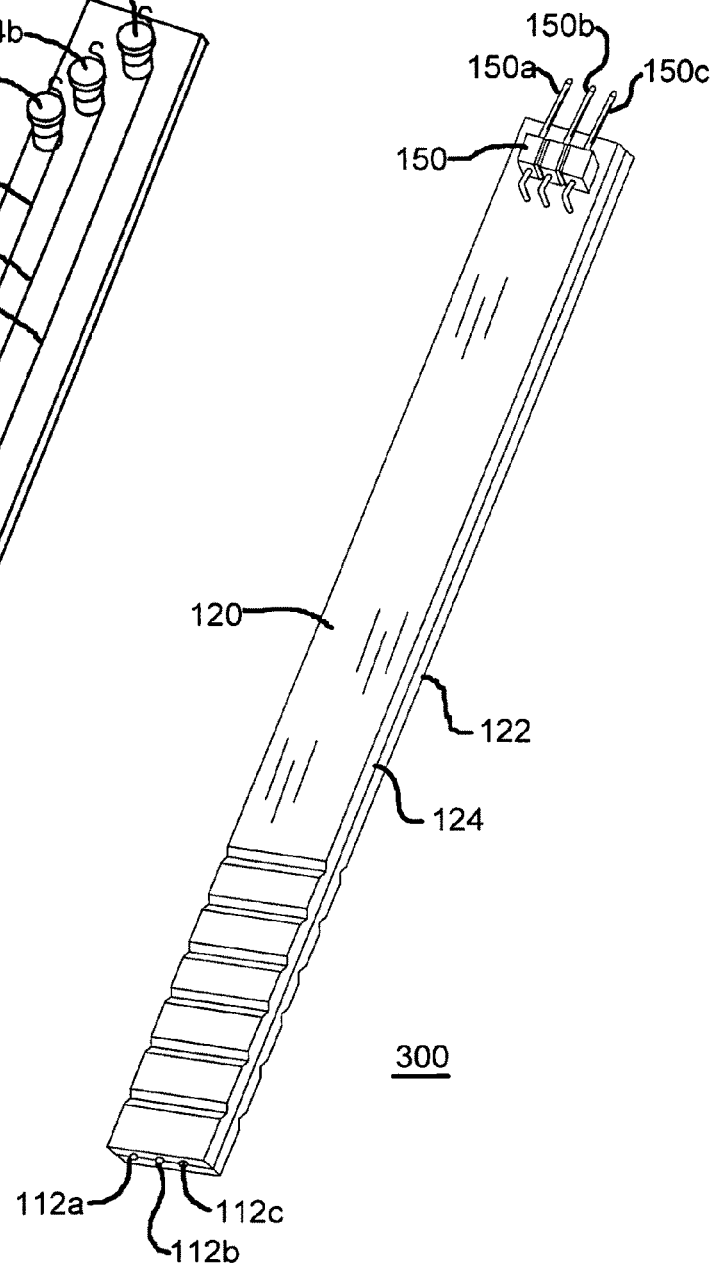

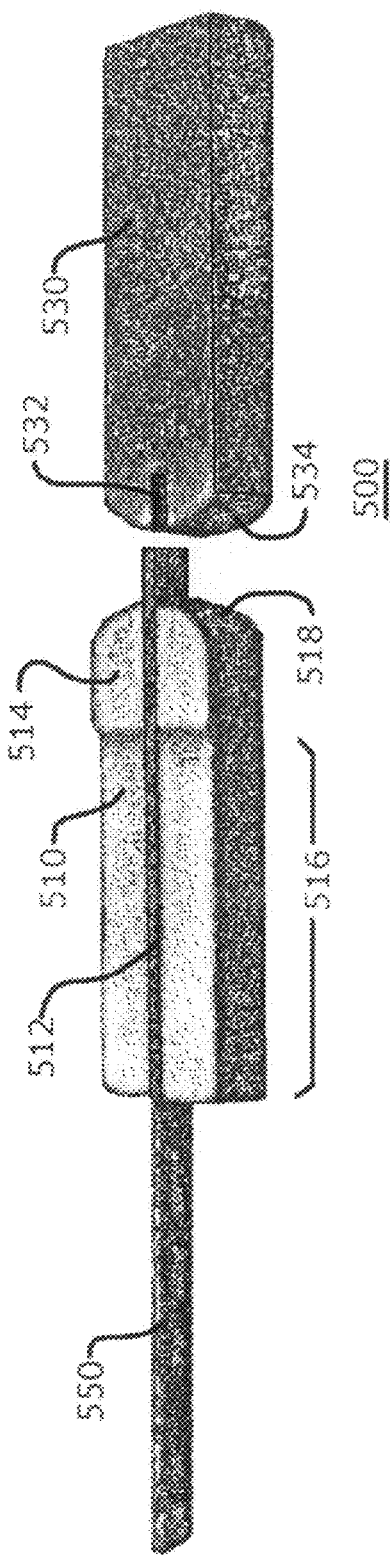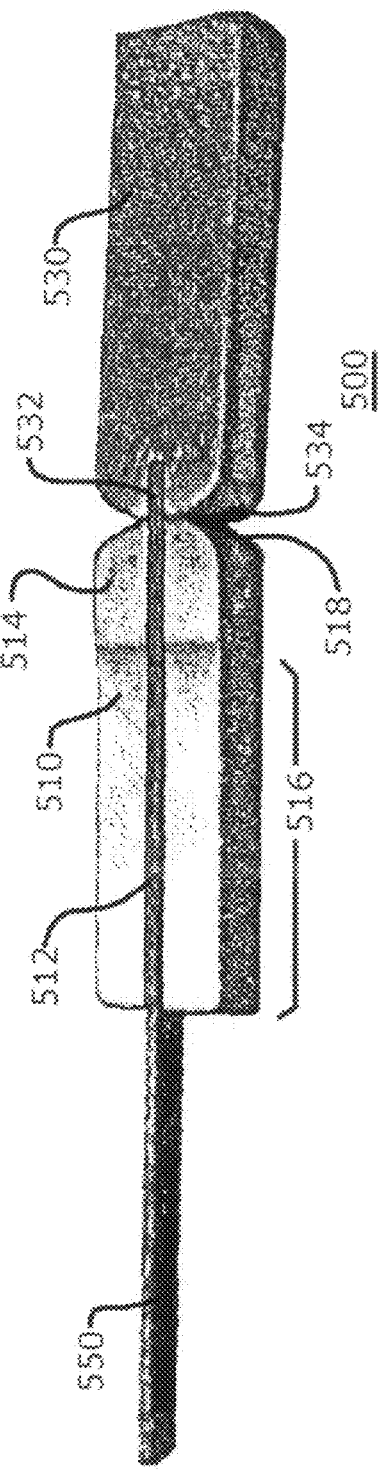

TOOL FOR SENSOR ARRANGEMENT WITH SNAP-OFF SEGMENTS

RELATIONSHIP TO OTHER APPLICATIONS

This application is a continuation, and claims the benefit of the filing date, of International Patent Application Ser. No. PCT/US2010/003145 filed on Dec. 10, 2010, which claims the benefit of the filing date of Provisional Patent Application Ser. No. 61/283,996 filed on Dec. 10, 2009, Conf. No. 6390 (Foreign Filing License Granted) in the names of the same inventor as herein. The disclosure in the identified PCT and United States Provisional Patent Applications are incorporated herein by reference.

BACKGROUND OF THE INVENTION

1. Field of the Invention

This invention relates generally to sensors, such as the type used to perform volammetric analysis, and more particularly, to a tool for use with a sensor arrangement having snap-off segments whereby one or more electrodes of the sensor are renewed.

2. Description of the Related Art

Electroanalytical methods are used in experimental analytical chemistry, and in multiple types of industrial processes. One such electroanalytical method is known as "voltammetry," wherein the characteristics of an analyte are learned by measuring current as voltage is varied. Systems employed in voltammetric experimentation typically require at least two electrodes. On such electrode is termed the "working electrode," which communicates with the analyte and applies the desired potential. The voltage is applied in accordance with a predetermined pattern wherein the transfer of electrons through the analyte is facilitated. Such voltage patterns include ramps (linear sweep), timed steps, square waves, and alternating sinusoidal and other cyclic voltage functions.

There is additionally provided in known electroanalytical systems a second electrode that functions as the other half of the cell. The second electrode is characterized with a known potential that is used to gauge the potential of the working electrode. In addition, the second electrode, in some systems, balances the electrons that have been added to, or removed from, the analyte by the working electrode. One significant issue with this known arrangement is that it is difficult to maintain a constant potential at the second electrode while passing current therethrough in an effort to counter the redox events taking place at the working electrode.

On known effort to overcome the forgoing difficulty involves the dividing of the functions of supplying electrons and of simultaneously providing a reference potential between two separate electrodes. In such an arrangement, the reference electrode constitutes a half cell having a known potential, and its role is limited to function as a reference in measuring and controlling the voltage of the working electrode. More specifically, it does not conduct any current. A separate auxiliary electrode passes all of the current that would be required to balance the current observed at the working electrode. In use, the auxiliary electrode (also known as a "counter electrode") will experience extensive variations in it voltage, often to the extreme potentials associated with the analyte under consideration. At such extreme voltages, the analyte, which may be a solvent or and electrolyte, is oxidized, or "reduced."

It is necessary that the working electrode have known dimensions and surface characteristics, and that it be cleaned and polished regularly. Such is not the case with the auxiliary electrode, which can be formed of a material that is conductive and that will not react with the analyte solution, or at least not the bulk analyte that has been added to reduce the overall resistance of the solution and thereby serves to improve accuracy.

As noted, there is a need to maintain the electrode clean. This creates a collateral need for a sensor arrangement that is inexpensive and does not need to be replaced simply because the electrode has become contaminated.

There is additionally a need in the art for a sensor system that facilitates renewal of the working electrode without requiring the entire sensor to be discarded.

It is, therefore, an object of this invention to provide a sensor arrangement that is inexpensive.

It is another object of this invention to provide an inexpensive sensor arrangement in which the working electrode can easily and inexpensively be renewed.

It is also an object of this invention to provide a simple sensor arrangement wherein the working electrode can easily be renewed without complex associated systems, as is the case, for example, in dropping mercury sensor systems.

SUMMARY OF THE INVENTION

The foregoing and other objects are achieved by this invention which provides a tool for a sensor arrangement. In accordance with the invention, the tool includes a first tool portion having an elongated channel extends that completely therealong for accommodating the sensor arrangement. A second tool portion has an end slot that accommodates therein an end portion of the sensor arrangement. In the practice of the invention, the sensor arrangement is provided with first and second substrates that are arranged in juxtaposed relation to each other, and a wire electrode embedded between the first and second substrates. At least one of the first and second substrates has transaxial scoring for facilitating the snapping off of segments of the first and second substrates to expose a clean portion of the wire electrode.

In one embodiment of the invention, a selectable one of said first and second tool portions is provided with a rounded end portion. In other embodiments, both of the first and second tool portions are provided with a rounded end portions.

In a further embodiment, the end slot of the second tool portion is dimensioned to correspond to an axial dimension of a segment that is to be snapped off from the sensor arrangement.

Preferably, the first tool portion has a shoulder portion and a handle portion. The shoulder portion has a greater thickness than the handle portion. In such an embodiment, the handle portion has a thickness that is less than a width dimension of the sensor arrangement.

In the practice of on embodiment the invention, the wire electrode is formed of gold. In other embodiments, there is provided a second electrode interposed between the first and second substrates of the sensor arrangement.

In accordance with a further apparatus aspect of the invention, there is provided a tool for use with a sensor, the sensor being of the type having an elongated wafer substrate with a predetermined width dimension and a predetermined thickness dimension. In this further apparatus aspect, the tool is provided with a first tool portion having an elongated channel that extends completely therealong for accommodating the predetermined thickness dimension of the sensor. The first tool portion is further provided with shoulder and handle portions, the shoulder portion having a thickness dimension that corresponds to the predetermined width dimension of the sensor. There is additionally provided a second tool portion having an end slot that accommodates therein an end portion of the sensor arrangement. The end slot is dimensioned to accommodate the predetermined thickness dimension of the sensor.

In one embodiment of this further apparatus aspect, the first tool portion is provided with a substantially rounded end portion in the vicinity of the shoulder portion. In another embodiment, the second tool portion is provided with a substantially rounded end portion in the vicinity of the end slot. Of course, in some embodiments, each of the first and second tool portions has a rounded end portion.

In a still further embodiment of the invention, the sensor is provided with a break-away portion having a predetermined length, and the end slot of said second tool portion has a depth dimension that corresponds to the predetermined length of the break-away portion. In this manner, the tool of the present invention will snap off the break-away portion of the sensor at a determined point along its length.

The tool of the present invention is particularly suite for use in connection with a sensor arrangement that has first and second substrates arranged in juxtaposed relation to each other. A working electrode is interposed between the first and second substrates. At least one of the first and second substrates has transaxial scoring for facilitating the snapping off of segments of the first and second substrates to expose a clean portion of the working electrode.

BRIEF DESCRIPTION OF THE DRAWING

Comprehension of the invention is facilitated by reading the following detailed description, in conjunction with the annexed drawing, in which:

FIG. 4 is a simplified schematic representation of an arrangement that is useful in the production of an embodiment of the invention that has a plurality of electrode wires;

FIG. 5 is a simplified schematic representation of a multi-electrode sensor arrangement having snap-off segments for renewing the working electrode in accordance with the principles of the present invention;

FIG. 6 is a simplified schematic representation of an arrangement that is useful in the production of an embodiment of the invention that has three electrode wires;

FIG. 7 is a simplified schematic representation of a multi-electrode sensor arrangement having snap-off segments for renewing the three working electrodes of FIG. 6 in accordance with the principles of the present invention;

FIG. 8 is a perspective representation of a two-part tool for snapping off cleanly the snap-off segments of the multi-electrode sensor arrangement of the present invention;

FIG. 9 is a perspective representation of the two-part tool for snapping off cleanly the snap-off segments of the multi-electrode sensor arrangement of the present invention shown in FIG. 9, wherein the multi-electrode sensor arrangement is engaged with both parts of the two-part tool;

DETAILED DESCRIPTION

Figure 1:
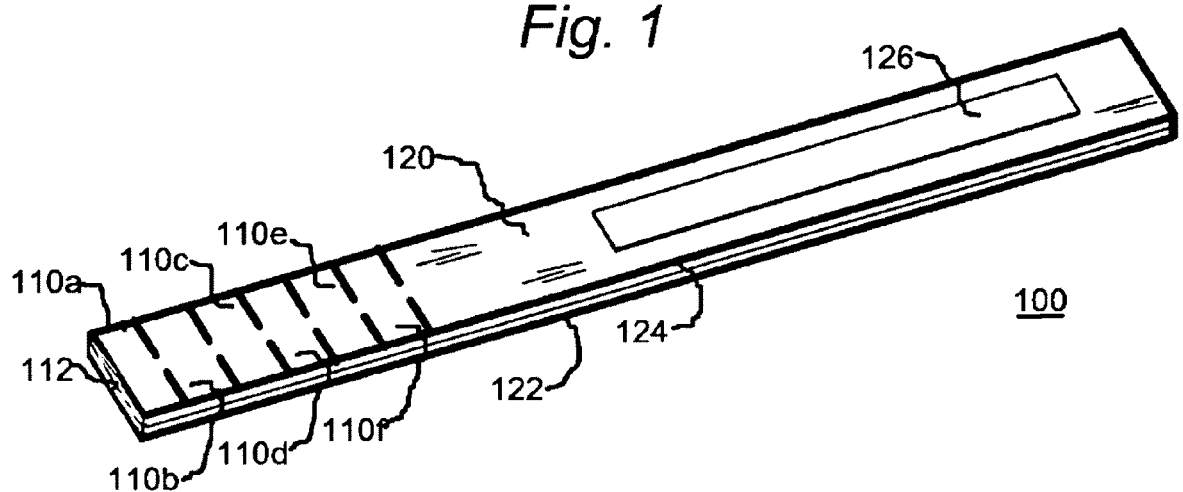
FIG. 1 is a simplified schematic representation of a sensor arrangement having snap-off segments for renewing the working electrode in accordance with the principles of the present invention.

FIG. 1 is a simplified schematic representation of a sensor arrangement 100 having snap-off segments 110a through 110f, in this specific illustrative embodiment of the invention, for renewing a working electrode 112. In this figure, the working electrode appears as but a dot and, in this specific illustrative embodiment of the invention, is shown as the cross-section of a wire, as will be discussed below in relation to FIGS. 2 and 3.

The wire of the present embodiment that constitutes working electrode 112 is interposed between substrates 120 and 122. The two substrates are disposed in juxtaposition along a juncture 124. In one embodiment, substrates 120 and 122 are respective printed circuit boards formed of conventional materials, such as polytetrafluoroethylene, phenolic cotton paper, cotton paper and epoxy, woven glass and epoxy, woven glass and polyester, matte glass and polyester, etc. Each of the substrates has deposited thereon an electrode. In the case of substrate 120, there is deposited a silver pad 126 that serves as an electrode. Substrate 122 in this specific illustrative embodiment of the invention bears thereon a gold pad 128 (not shown in FIG. 1, see, FIG. 2) that also serves as an electrode. It is to be understood that in some embodiments of the invention, silver pad 126 and/or gold pad 128 can extend over the entire length to sensor arrangement 100, whereby a three-electrode system is renewed at the working tip.

Illustratively, the sensor of this particular embodiment comprises a sensor wire 112 that extends throughout the length of sensor arrangement 100. The sensor wire may comprise any known metal or combination of metals, such as gold, platinum, gold/mercury, iridium, iridium/mercury, etc. While the sensor is shown here as a wire, it is to be understood that the sensor may be in any known form, such as an individual sensor or an array of sensors, formed by any technique such as screen-printing, lithography, or various deposition techniques. Potentiometric and voltammetric sensors are included within the scope of the present invention.

As sensor arrangement 100 is employed in use in an analyte (not shown), the working electrode becomes fouled resulting in inaccuracy and eventual near total loss of functionality. In accordance with the invention, the working electrode is renewed by snapping off segment 110a at the associated score mark (shown as a dashed line, not specifically designated), thereby presenting a clean portion of working electrode 112 to the analyte. Once the portion of the working electrode disposed at the proximal end of segment 110a becomes fouled, then segment 110b is removed exposing an additional clean portion of the working electrode. In this specific illustrative embodiment of the invention, this process is continued until segment 110f is snapped off, and once the clean portion of the working electrode proximal to segment 110f becomes fouled, the sensor is discarded. Thus, the useful life of an already inexpensive sensor arrangement is greatly extended.

Traditionally the working electrode always has been polished to create a mirrored surface and to clean it before the next analysis. It is expected that a clean surface provides reproducible results as recorded in a voltammetric curve known in the art as a "voltammogram." The conventional cleaning of the surface of the electrode could in some instances be problematical as the surface of the electrode might be changed as it is modified (i.e., polished) with the abrasive materials (not shown) that are commonly used in the cleaning process, specifically diamond or alumina of different grit sizes. The present invention, however, provides a clean surface every time a segment is removed by snapping same off. The resulting surface might be irregular, but it will be clean. Basic qualitative analysis can be performed with such a surface, and if a quantitative analysis is required, standard curves can be made for determination of concentration. It is to be understood, however, that although the electrode of the present invention is intended for analytical sensor work, the sensor can be treated and polished in the conventional manner.

In some embodiments of the invention, the electrode surface is renewed, as herein described, preferably by snapping of segments of the electrode. However, in other embodiments, the electrode can be renewed by cutting, cleaving, or polishing. Although difficulty might arise when endeavoring to polish an entire multiple electrode system, one is nevertheless assured that the snapping off of electrode segments will result in a clean electrode surface.

A voltammogram represents results measured from an electrochemical cell (not shown), having three electrodes. These are, the reference electrode, the working electrode, and the counter electrode. The potential (voltage) is applied between the working and reference electrodes, and the responsive current is measured between the working electrode and the counter electrode.

The measurement of the current needs to be accurate and precise, and is responsive to the cross sectional area of the electrode to be the same. In addition, the measurement must itself be reproducible. This is effected by contamination (i.e., poisoning) of the electrode surface. Certain materials of chemical ions or species can become attached to the surface and not come off the surface when the electrode is used (voltage scanned). Such poisoning of the surface affects the overall current measured.

Electrochemists have used various techniques to clean the electrode between runs without the need for polishing. One such electrochemical technique cleans the electrode surface by pulse cleaning, whereby the potential is driven into an oxidative potential and then into a reductive potential before the electrode is used again. This technique pushes the contaminants off of the surface oxidatively, and then the potential of interest is applied to record a current, or the potential is scanned and the resulting variation in the current is observed as a voltammogram. However, when the electrode cannot be renewed in this simple fashion more aggressive steps, such as polishing or snapping off of a segment in accordance with the invention, are required.

In embodiments of the invention that are intended for extended use, mechanisms may be employed (not shown) that automatically snap off the electrode segments to renew the electrode when required. The need for electrode renewal would become apparent when the data collected on periodic standard solutions (not shown) varies.

In a specific illustrative embodiment of the invention, sensor arrangement 100 is approximately 5" long (including the snap-off segments) and ¼" wide. Each of the snap-off segments is approximately ¼" long along the principal axis (not specifically designated). However, it is understood that these dimension are merely illustrative, and any other suitable dimensions can be employed in the practice of the invention. In some embodiments of the invention, the width of the sensor arrangement is responsive to the number of wires therewithin.

Figure 2:
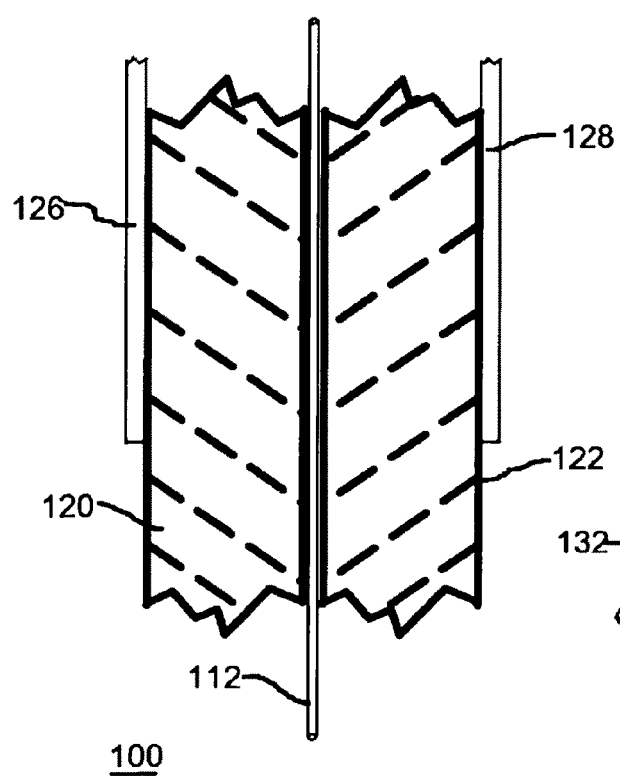
FIG. 2 is a simplified cross-sectional schematic representation of a portion of the embodiment of the invention illustrated in FIG. 1.

FIG. 2 is a simplified cross-sectional schematic representation of a portion of sensor arrangement 100 illustrated in FIG. 1, the representation of FIG. 2 being significantly enlarged to reveal the internal structure of the sensor arrangement of the present embodiment of the invention. Elements of structure that have previously been discussed are similarly designated. As shown in this figure, working electrode 112, in this specific illustrative embodiment of the invention, is a gold wire that, as previously indicated, is interposed between substrates 120 and 122. In some embodiments of the invention the working electrode, rather than being in the form of a wire as shown herein, is printed on, or deposited onto, one or both of the substrates. More that one such working electrode (not shown in this figure) can easily be employed in the practice of the invention, while maintaining the significant advantage achieved by the snapping off of sensor segments to renew multiple working electrodes simultaneously. Also, different working materials can be employed within a single sensor.

As previously noted, silver pad 126 is disposed on substrate 120. This figure shows a specific illustrative embodiment of the invention wherein a gold pad 128 is disposed on substrate 122.

Figure 3:
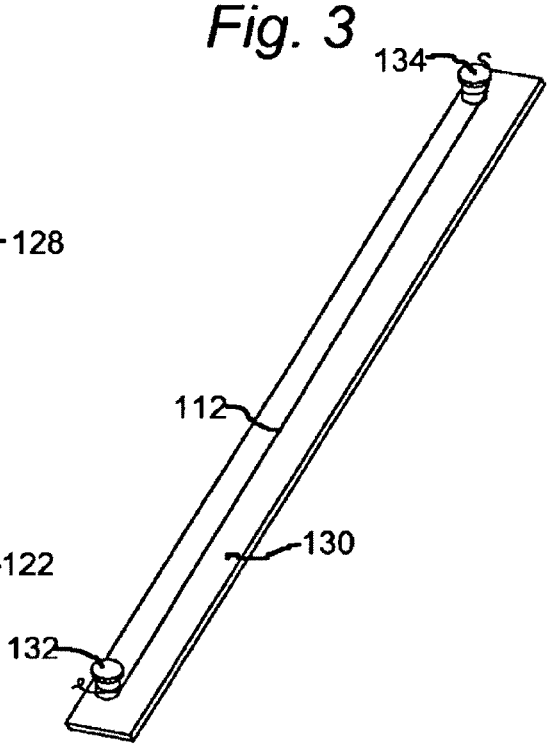
FIG. 3 is a simplified representation of an arrangement that is useful in the production of a specific illustrative embodiment of the invention.

FIG. 3 is a simplified representation of an arrangement that is useful in the production of a specific illustrative embodiment of the invention. As shown in this figure, a substrate 130 is provided with studs 132 and 134 about which are wound gold wire 112. An adhesive (not shown) is then deposited over the substrate and the gold wire, and a second substrate (not shown) is placed over substrate 130 whereby gold wire is disposed between the substrates. In the practice of this aspect of the invention, the overall length of substrate 130 is approximately 6".

In some embodiments of the invention, one of the substrates is provided with an axial channel (not shown) that accommodates the gold wire. In other embodiments, the working electrode is deposited or printed onto the substrate. Multiple gold wires or other working material can be printed or deposited as working electrodes within a single sensor arrangement within the scope of the present invention.

FIG. 4 is a simplified schematic representation of an arrangement that is useful in the production of an embodiment of the invention that has a plurality of electrode wires, specifically electrode wires 112a and 112b. Elements of structure that have previously been discussed are similarly designated. In a specific illustrative embodiment of the invention, one or both of electrode wires 112a and 112b are made of gold. However, other suitable electrode materials, such as silver, platinum, and the like, can be used in the practice of the invention.

The invention is not limited to the numbers of electrode wires (or conductors) shown in the figures. Moreover, the working electrodes are not limited in the practice of the invention to wires, and may be formed by any of several known printing or deposition processes.

FIG. 5 is a simplified schematic representation of a multi-electrode sensor arrangement 200 having snap-off segments as hereinabove described for renewing a plurality of working electrodes in accordance with the principles of the present invention. Elements of structure that have previously been discussed are similarly designated. In this embodiment of the invention, two working electrode wires 112a and 112b are disposed between substrates 120 and 122. As described above in relation for FIG. 1, the working electrodes are renewed by snapping off segments. The snap-off segments are shown to be separable at regions of reduced substrate thickness, but are not specifically designated in this figure. As shown in this figure, working electrode wires 112a and 112b extend beyond the distal end of substrates 120 and 122 to facilitate electrical connection to a monitoring system (not shown).

FIG. 6 is a simplified schematic representation of an arrangement that is useful in the production of an embodiment of the invention that has three electrode wires. Elements of structure that have previously been discussed are similarly designated. In this specific illustrative embodiment of the invention, electrode wires 112a, 112b, and 112c are formed of gold silver, and platinum electrode materials, respectively.

FIG. 7 is a simplified schematic representation of a multi-electrode sensor arrangement 300 having snap-off segments for renewing the three working electrodes of FIG. 6 in accordance with the principles of the present invention. Elements of structure that have previously been discussed are similarly designated. In this embodiment, the entire three-electrode system, which would constitute in some embodiments the working and reference electrodes, is renewable at the tip. Thus, silver pad 126 and gold pad 128 are not necessary, depending upon the intended application.

There is additionally shown in this embodiment of the invention a terminal block 150 that facilitates the electrical communication between the working electrode wires and monitoring equipment (not shown). In some embodiments, conductive pads (not shown) are used instead of a terminal block to provide electrical access to the electrode wires. In the present embodiment, working electrode wires 112a, 112b, and 112c communicate electrically with respectively associated ones of terminals 150a, 150b, and 150c, of terminal block 150.

It is to be understood that the multi-electrode sensor arrangement of the present invention is not limited to the substantially rectangular cross-sectional configurations illustrated in the foregoing figures as multi-electrode sensor arrangements 100, 200, and 300. The multi-electrode sensor arrangements can be configured to have any cross-sectional shape including, for example, a round, oval, or polygonal cross-sectional configuration.

In addition, the multi-electrode sensor arrangement bodies can be formed of any of a variety of materials, including, for example, a polymer or plastic material, or polyetheretherketone (PEEK), or a ceramic material, such as alumina oxide, which typically contains about 70-80% aluminum oxide and small amount of silica ($SiO_2$), MgO, and zirconia ($ZrO_2$). Such ceramic materials have excellent electrical insulating properties.

FIG. 8 is a perspective representation of a two-part tool 500 formed of tool portion 510 and tool portion 530 for snapping off cleanly the snap-off segments (not specifically designated) of multi-electrode sensor arrangement 550. Multi-electrode sensor arrangement 550 is configured in accordance with the inventive sensor described herein in relation to FIGS. 1-7. Two-part tool 500 is particularly adapted for achieving a clean break in multi-electrode sensor arrangement 550 which, as described hereinabove, employs a wire electrode (not specifically designated in this figure). It is an advantage of the use of two-part tool 500 that the clean break of the snap-off segments (not specifically designated) results in cross-sectionally consistent presentation of the wire electrode with each renewal of multi-electrode sensor arrangement 550. This ensures consistent and repeatable analytical results as multi-electrode sensor arrangement 550 is renewed.

FIG. 8 additionally shows that tool portion 510 is provided with an elongated channel 512 that accommodates multi-electrode sensor arrangement 550. Tool portion 530 has a relatively short slot 532 the accommodates a segment of multi-electrode sensor arrangement 550 that is to be snapped off. In a highly advantageous embodiment of the invention, slot 532 has an axial depth dimension that is consistent with the dimension of the snap-off segment (not specifically designated in this figure).

FIG. 9 is a perspective representation of the two-part tool for snapping off cleanly the snap-off segments of the multi-electrode sensor arrangement of the present invention shown in FIG. 9, wherein the multi-electrode sensor arrangement is engaged with both parts of the two-part tool. Elements of structure that have previously been discussed are similarly designated.

Tool portion 510 is shown in FIGS. 8 and 9 to have a shoulder portion 514 having a thickness that is dimensioned to conform to the width of multi-electrode sensor arrangement 550. Tool portion 530, at least in the region of slot 532, has a similar thickness. Thus, the width of multi-electrode sensor arrangement 550 is fully accommodated in shoulder portion 514 and in slot 532 of tool portion 530. Tool portion 510 is further shown to have a handle portion 516 that is, in this embodiment of the invention, formed integrally with shoulder portion 514. Handle portion 516 is not as deep as shoulder portion 514, and therefore multi-electrode sensor arrangement 550 protrudes therefrom so as to enable multi-electrode sensor arrangement 550 to be held in place by the hand of the user, as will be described below in connection with FIGS. 10 and 11.

Tool portion 510 is shown to have a rounded end portion 518. Similarly, tool portion 530 has a rounded end portion 534. As will be described below in connection with FIG. 12, the rounded portions facilitate the snapping-off action whereby a segment of multi-electrode sensor arrangement 550 (not specifically designated in this figure) is snapped off and the electrode is renewed by exposing unused cross-sectional portions of the electrode wire(s) (not shown in this figure).

Figure 10:
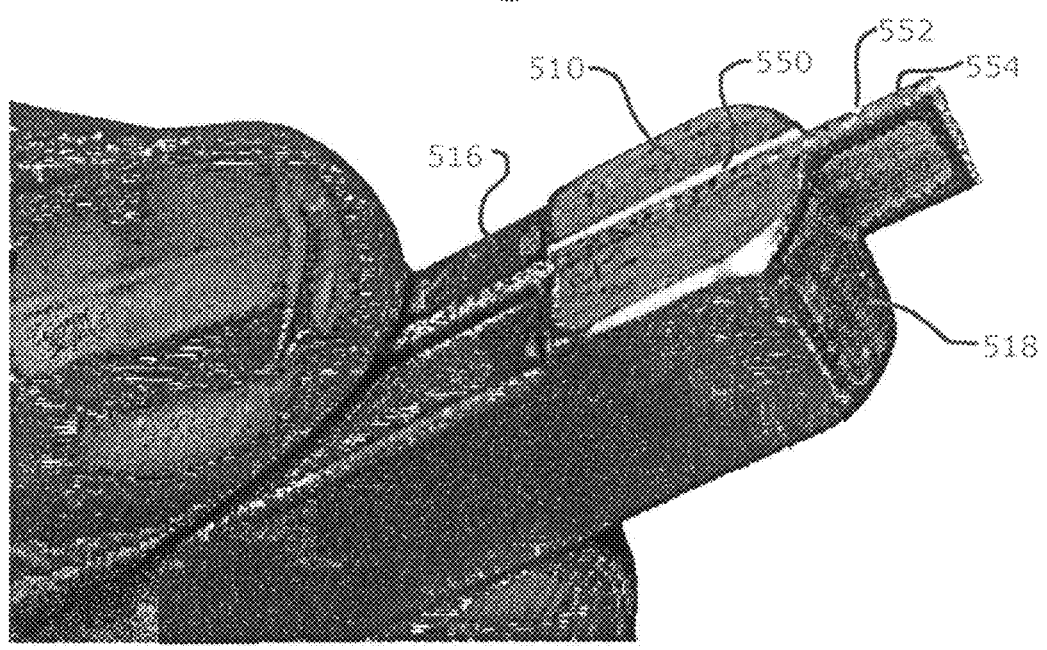
FIG. 10 is a perspective representation of a first portion of the two-part tool, this figure showing the early steps involved in manipulation of the tool.

FIG. 10 is a perspective representation of tool portion 510 of the two-part tool with multi-electrode sensor arrangement 550 extending axially therefrom. Elements of structure that have previously been discussed are similarly designated. This figure represents an initial step in the use of the tool of the present invention. As shown in this figure, multi-electrode sensor arrangement 550 is installed in tool 510, and the portion of multi-electrode sensor arrangement 550 that extends outward of handle portion 516 communicates with the hand of the user (not specifically designated). Multi-electrode sensor arrangement 550 is shown to have a transaxial score 552 that facilitates the snapping off of sensor segment 554. IN this specific illustrative embodiment of the invention, multi-electrode sensor arrangement 550 is scored with transaxial score 552 on only one side. In other embodiments, however, multi-electrode sensor arrangement 550 can be scored on both sides, as shown in FIGS. 5 and 7.

Figure 11:
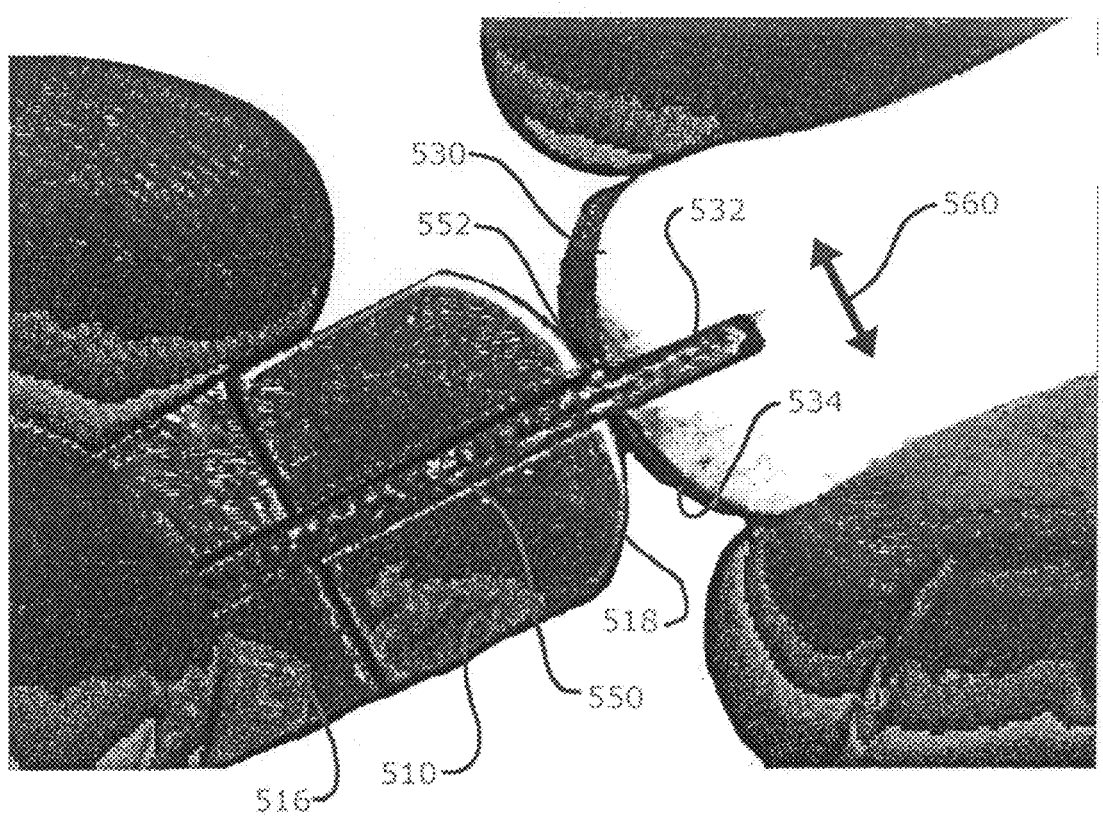
FIG. 11 is a perspective representation of the first and second portions of the two-part tool, this figure showing an intermediate step involved in manipulation of the tool.

FIG. 11 is a perspective representation of the first and second portions of the two-part tool, this figure showing an intermediate step involved in manipulation of the tool. Elements of structure that have previously been discussed are similarly designated. As shown in this figure, slot 532 of tool portion 530 is dimensioned such that transaxial score 552 is disposed precisely where tool portions 510 and 530 communicate with one another, at their respective rounded portions 518 and 534. Thus, when tool portion 530 is manipulated several times in the directions of two-headed arrow 560, rounded portion 518 and 534 essentially roll against one another, flexing multi-electrode sensor arrangement 550 at transaxial score 552, whereby fatiguing results at the score and the snap-off action occurs.

Although the invention has been described in terms of specific embodiments and applications, persons skilled in the art can, in light of this teaching, generate additional embodiments without exceeding the scope or departing from the spirit of the invention described and claimed herein. Accordingly, it is to be understood that the drawing and description in this disclosure are proffered to facilitate comprehension of the invention, and should not be construed to limit the scope thereof.

What is claimed is:

1. A combination of a tool and a sensor comprising:
a first tool portion having an elongated channel extending completely therealong for accommodating the sensor;
a second tool portion having an end slot for accommodating therein an end portion of the sensor;
wherein the sensor further comprises:
first and second substrates arranged in juxtaposed relation to each other; and
a wire electrode disposed between the first and second substrates;
wherein at least one of the first and second substrates has transaxial scoring for facilitating the snapping off of segments of said first and second substrates to expose a clean portion of the wire electrode.

2. The tool of claim 1, wherein a selectable one of said first and second tool portions is provided with a rounded end portion.

3. The tool of claim 2, wherein said first and second tool portions are each provided with a rounded end portion.

4. The tool of claim 1, wherein the end slot of said second tool portion is dimensioned to correspond to an axial dimension of a segment that is to be snapped off from the sensor.

5. The tool of claim 1, wherein said first tool portion has a shoulder portion and a handle portion, the shoulder portion having a greater thickness than the handle portion.

6. The tool of claim 5, wherein the handle portion has a thickness that is less than a width dimension of the sensor.

7. The tool of claim 1, wherein the wire electrode is comprised of gold.

8. The tool of claim 1, wherein there is further provided a second electrode interposed between said first and second substrates of the sensor.

9. A renewable electrode arrangement comprising:
a sensor having an elongated wafer substrate with a predetermined width dimension and a predetermined thickness dimension and also having a break-away portion that exposes the electrode, the electrode being disposed in juxtaposed relation to the elongated wafer substrate;
a first tool portion having an elongated channel extending completely therealong for accommodating the predetermined thickness dimension of the sensor, said first tool portion having shoulder and handle portions, the shoulder portion having a thickness dimension that corresponds to the predetermined width dimension of the sensor; and
a second tool portion having an end slot for accommodating therein an end portion of the sensor, the end slot being dimensioned to accommodate the predetermined thickness dimension of the sensor.

10. The tool of claim 9, wherein said first tool portion is provided with a substantially rounded end portion in the vicinity of the shoulder portion.

11. The tool of claim 9, wherein said second tool portion is provided with a substantially rounded end portion in the vicinity of the end slot.

12. The tool of claim 9, wherein the break-away portion has a predetermined length, and the end slot of said second tool portion has a depth dimension that corresponds to the predetermined length of the break-away portion.

* * * * *